United States Patent [19]

Chou et al.

[11] 4,303,591

[45] Dec. 1, 1981

[54] REMOVAL OF STANNIC CHLORIDE

[75] Inventors: Ta-sen Chou; Perry C. Heath, both of Indianapolis; Wayne D. Luke, West Lafayette, all of Ind.

[73] Assignee: Eli Lilly and Company, Indianapolis, Ind.

[21] Appl. No.: 166,004

[22] Filed: Jul. 7, 1980

[51] Int. Cl.$^3$ .............................................. C07F 7/22
[52] U.S. Cl. .................................. 260/429.7; 210/729
[58] Field of Search ...................... 260/429.7; 210/729

[56] References Cited

U.S. PATENT DOCUMENTS 3,461,132  8/1969  Schröder et al. ................. 260/429.7
3,471,250  10/1969  Langer .............................. 260/429.7

OTHER PUBLICATIONS

Lappert and Smith, J. Chem. Soc., 3224–3230 (1961), "Reactions of Sulphoxides with Some Group III and IV Halides.

Cotton and Francis, J. Am. Chem. Soc. 82, 2986–2991 (1960) "Sulfoxides as Ligands, I. A Preliminary Survey of Methyl Sulfoxide Complexes".

*Primary Examiner*—Jacqueline V. Howard
*Attorney, Agent, or Firm*—Joseph A. Jones; Arthur R. Whale

[57] ABSTRACT

Stannic chloride is removed from organic solvent-based waste streams by precipitating the salt as a dimethyl sulfoxide complex.

6 Claims, No Drawings

REMOVAL OF STANNIC CHLORIDE

BACKGROUND OF THE INVENTION

1. Field of the Invention

This invention belongs to the field of waste disposal and pollution control, and provides a method of removing stannic chloride from organic solvent-based waste streams. The compound is removed by forming an insoluble complex of it with dimethyl sulfoxide and separating the complex from the waste stream.

The objective of the present invention is to provide an economical and convenient process for the removal of stannic chloride from organic solvent-based waste streams, in order both to recover the compound for reuse, and to free the waste stream of it. It is well known that tin is in short supply and expensive, and accordingly an economical way to recover it is advantageous. Further, compounds such as stannic chloride are regarded as pollutants when contained in waste streams, and interfere with solvent recovery,

2. State of the Art

Complexes of sulfoxides and stannic chloride are known in the literature, and their physical chemistry has been studied. See, for example, Lappert and Smith, *J. Chem. Soc.* 3224-30 (1961), and Cotton and Francis, *J. Am. Chem. Soc.* 82, 2986-91 (1960).

SUMMARY OF THE INVENTION

This invention provides a process for removing stannic chloride from solutions thereof in organic solvent-based waste streams, wherein the solvent is benzene; benzene mono- or disubstituted with $C_1$-$C_3$ alkyl, chloro, bromo, $C_1$-$C_2$ alkoxy or nitro; benzene monosubstituted with $C_1$-$C_5$ alkoxycarbonyl, benzyloxycarbonyl, phenoxycarbonyl or acetyl; $C_1$-$C_5$ alkanol; $C_1$-$C_4$ alkane monosubstituted with $C_2$-$C_5$ alkanoyl, nitro or $C_2$-$C_3$ alkanoyloxy; acetonitrile; or $C_5$-$C_8$ cycloalkanone; mixtures of said solvents; or a mixture of one or more of said solvents with a minor amount of a $C_5$-$C_{10}$ alkane; which process comprises adding to the waste stream from about 2 to about 4 moles of dimethyl sulfoxide (DMSO) per mole of stannic chloride, and separating the resulting precipitate of dimethyl sulfoxide-stannic chloride complex from the waste stream.

DESCRIPTION OF THE PREFERRED EMBODIMENT

It has been found that the present invention is useful for removing stannic chloride from an extremely wide variety of organic solvents. For example, the compound may be removed by this invention from waste streams made up of the following solvents, individually or in combination.

benzene
toluene
p-xylene
o-xylene
ethylbenzene
methanol
ethanol
propanol
isobutanol
acetone
methyl ethyl ketone
diethyl ketone
dipropyl ketone
dibutyl ketone
methyl isobutyl ketone
cyclohexanone
cycloheptanone
chlorobenzene
1,3-dichlorobenzene
propylbenzene
bromobenzene
1,2-dibromobenzene
1,4-diethylbenzene
methoxybenzene
ethoxybenzene
1,3-diethoxybenzene
1,4-dimethoxybenzene
nitrobenzene
methyl benzoate
isopropyl benzoate
pentyl benzoate
benzyl benzoate
phenyl benzoate
acetophenone
isopentanol
neopentanol
methyl propyl ketone
nitromethane
nitroethane
nitrobutane
methyl acetate
ethyl acetate
isopropyl acetate
isobutyl acetate
amyl acetate
neopentyl acetate
propyl propionate
t-butyl propionate
cyclopentanone
acetonitrile As has been stated, the solvent may contain a minor amount of a $C_5$-$C_{10}$ alkane, such as a pentane, hexane, heptane, octane, nonane or decane. By the term "a minor amount" is meant up to about 25% by volume of the solvent.

Certain classes of solvents are preferred as the media in which to carry out the process of this invention. The following are preferred classes.

(1) benzene; benzene mono- or disubstituted with $C_1$-$C_3$ alkyl, chloro, bromo, $C_1$-$C_2$ alkoxy or nitro;
(2) $C_1$-$C_5$ alkanols;
(3) $C_1$-$C_4$ alkane monosubstituted with $C_2$-$C_5$ alkanoyl; $C_5$-$C_8$ cycloalkanones; acetophenone;
(4) benzene monosubstituted with $C_1$-$C_5$ alkoxycarbonyl, benzyloxycarbonyl or phenoxycarbonyl; $C_1$-$C_4$ alkane monosubstituted with $C_2$-$C_3$ alkanoyloxy.

It has been found that organic contaminants dissolved in the solvent-containing waste stream have no adverse effect or very slight adverse effect on removal of stannic chloride according to this invention. The source and exact composition of the waste steams are not significant in the practice of this invention, and it may be used on any stannic chloride-containing organic solvent based waste. Naturally, the waste stream should be essentially free of suspended solids before the dimethyl sulfoxide is added, so that the DMSO-stannic chloride precipitate may be separated by filtration or the like, free of other solids.

A particularly advantageous use of the process of this invention has been found in the removal of stannic chloride from the liquid waste emanating from a process described by Chou in U.S. Pat. No. 4,190,724 and Kukolja in U.S. Pat. No. 4,052,387. The process provides a 3-exomethylenecephalosporin by ring-opening a penicillin, and re-closing the resulting sulfinyl chloride by treatment first with stannic chloride, and then with an alcohol. The desired cephalosporin precipitates, leaving the stannic chloride dissolved in the reaction mixture, which is composed in large part of the alcohol, with some aromatic solvent, some ether or ketone used as an adjuvant, and various organic substances left over from the reaction. It has been found that the process of this invention removes stannic chloride from this waste stream in essentially quantitative yield.

The temperature of the mixture in which the process of this invention isused is not critical to the efficiency of the process. It is preferred to carry the process out at ambient temperature, for convenience and economy. The term "ambient temperature" is used here to refer to the temperature of the environment in which the process is carried out, and is regarded as usually being in the range of from about 10° C. to about 35° C.

However, the process is operable at temperatures in the range of from about 0° C. to about 60° C., and may be carried out at such temperatures if it is convenient to do so in a given instance.

The concentration of stannic chloride in the waste stream is not critical to the success of this invention. The DMSO-stannic chloride complex will form even at very low concentrations of the compound, above about 1 g./liter of tin. The examples below illustrate the recovery of stannic chloride from solutions containing in the range of 5–15% by weight; it is recovered in the same manner from solutions containing as little as 1% by weight, or even less. Similarly, the upper limit of concentration of stannic chloride in the waste stream is limited only by its solubility in the solvent or solvents which make up the stream.

Waste streams containing stannic chloride are inherently acidic, since the compound is not stable in basic conditions. The degree of acidity of the waste stream is not important in the process of this invention, nor is the acidity of the waste stream changed by removing stannic chloride from it by this process.

Formation of the DMSO-stannic chloride complex is exothermic. The degree of the exotherm depends on the concentration of the stannic chloride, and on the solvent in the waste stream. In some cases it is necessary to cool the vessel, or to condense and reflux solvent vapor.

Formation of the complex is very rapid. Addition of DMSO to waste stream may be either slow or fast, as may be convenient, and the complex is formed and precipitates from the waste stream rapidly in either case. Only ordinary stirring is necessary to mix the DMSO through the waste stream. It has been found that the complex is formed in essentially the amount of time necessary to mix the DMSO homogeneously with the waste stream. In many experiments, the complex, once formed, has been allowed to stand in the waste stream for lengths of time up to a few days, without adverse effect on the amount of the compound removed from the waste stream. Thus, it appears that the complex is formed extremely rapidly, and that it does not re-dissolve after formation.

It is believed that the complex is composed of 1 mole of stannic chloride and 2 moles of DMSO.

Accordingly, if essentially complete removal of the compound is to be obtained, at least 2 moles of DMSO must be added to the waste stream for every mole of stannic chloride in it. Large excess amounts of DMSO have been found to reduce the removal of the compound, presumably by re-dissolving some of the complex. Therefore, it is advisable to use no more than 4 moles of DMSO per mole of stannic chloride in the waste stream. As has been pointed out, there is no advantage to using excess amounts of DMSO, since stannic chloride is essentially quantitatively precipitated as the complex when only approximately the theoretical 2 moles of DMSO is added. Accordingly, it is preferred to add at least about 2 moles of DMSO per mole of stannic chloride, and no more than about 4 moles.

No particular health hazards or pollution problems arise from the use of the present invention. It is well known that DMSO must be used cautiously, and instructions for its use are available.

The final step in the process of this invention is to separate the solid complex from the waste stream. The separation step has been carried out both by filtration and by centrifuging, both of which have been found to be easy and rapid.

Ordinarily, the separated complex will be processed to recover the tin value from it. Such recovery is relatively easy and economical. The theoretical tin content of the complex is 28.5%, and it has been found that the separated complex contains only 10–15% of entrained solvent. Therefore, the tin content of the recovered complex is high, and it may be economically burned to form oxides of tin, which may be further conventionally processed.

The DMSO-stannic chloride complex is identified by its infrared spectrum, which exhibits the following characteristics absorption bands:

3010 cm.$^{-1}$
3000
2920
1420 strong
1410
1395
1325 weak
1300 weak
1030 strong
985 very strong
945 strong
918 very strong
900 very strong
720 weak, broad
480 very strong, broad
325 very strong, broad The following examples further illustrate the use of this invention in removing stannic chloride from organic solvent-based waste streams.

EXAMPLE 1

A solution of stannic chloride was prepared by adding approximately 7 ml. of stannic chloride to a 200 ml. portion of methanol. To the solution was added 7 ml. of DMSO which had been dried over 4A molecular sieves. A white precipitate formed immediately, as the DMSO was added.

The solution was stirred at ambient temperature for 1 hour after the addition was complete, and the precipitate was separated by filtration. The filtrate was diluted to 250 ml. by addition of methanol, and was analyzed for tin. The methanol solution was found to contain 1450 ppm. by weight, equivalent to 4.7% of the original tin content.

The following example shows the use of stannic chloride in the preparation of a 3-exomethylene-cephalosporin, and the removal of the tin compounds from the waste stream from the process.

EXAMPLE 2

A 2-liter flask was equipped with a stirrer, a reflux condenser and a Dean-Stark trap, and was charged with 1 liter of toluene and 25 g. of poly-4-vinylpyridine. The slurry was heated to boiling, and the first 100 ml. of toluene collected was discarded to eliminate water. The suspension was then cooled, and 75 g. of 4-nitrobenzyl 6-phenoxyacetamido-2,2-dimethylpenam-3-carboxylate-1-oxide and 33.9 g. of N-chlorophthalimide were added, with a 100-ml. rinse or dry toluene. The reaction mixture was stirred at reflux temperature for 100 minutes, and was then cooled to 5°–10° C. over a 30 minute period. The cold mixture was then filtered, and the solids were rinsed with 100 ml. of toluene.

The brown filtrate was placed in a clean 2-liter flask, and was cooled to 5°–10° C. A 14 ml. portion of diethyl ether was added, followed by 37.5 ml. of stannic chloride. The mixture was stirred for 30 minutes at constant temperature, and then for 16 hours at ambient temperature. The mixture was then filtered. The solids were washed with 300 ml. of hexane, which was added to the filtrate.

The solids were then added to another flask, to which was added 450 ml. of dry methanol. The suspension was stirred for 4.25 hours at 5°–10° C., and was filtered. The solids were washed with 150 ml. of additional methanol, and dried overnight at 50° C. under vacuum. The yield was 46.45 g. of 4-nitrobenzyl 7-phenoxyacetamido-3-exomethylenecepham-4-carboxylate.

The toluene-hexane filtrate from the first isolation above was treated with 100 ml. of DMSO, affording a fine white precipitate, which was isolated by filtration and dried overnight at 50° C. The yield was 12.24 g. of DMSO-stannic chloride complex.

The methanol filtrate from the last isolation above was placed in a flask, and to it was added with stirring, dropwise, 25 ml. of DMSO. A white precipitate fromed, and was collected by filtration, washed with methanol and dried overnight to obtain 62.15 g. of DMSO-stannic chloride complex.

EXAMPLE 3

Two hundred and fifty ml. aliquots of methanol filtrate from a process similar to that described in Example 2 were treated with various amounts of DMSO, and the mixtures were stirred at ambient temperature for 1 hour. The precipitates of DMSO-stannic chloride complex were isolated by filtration, and the solids were washed with 50 ml. of methanol in each case and vacuum dried for 16 hours at 50° C. The amounts of complex were as follows.

| Amount of DMSO | Amount of complex |
|---|---|
| 5 ml. | 6.43 g. |
| 10 ml. | 21.61 g. |
| 15 ml. | 28.93 g. |
| 25 ml. | 31.18 g. |
| 50 ml. | 30.97 g. |
| 250 ml. | 10.76 g. |

EXAMPLE 4

A 250 ml. portion of methanol filtrate as described in Example 3 was mixed with 50 ml. of hexane, and to the solution was added, with stirring, 25 ml. of DMSO. A white precipitate formed immediately, and the suspension was stirred for 1 hour after the addition. The solids were then isolated by filtration, washed with methanol and dried at 50° C. for 16 hours. The yield was 31.07 g. of DMSO-stannic chloride complex.

EXAMPLE 5

This example reports a large-scale experiment, in which stannic chloride was recovered from 7580 liters of methanol filtrate, obtained from a large-scale synthesis similar to that described in Example 2.

The filtrate was analyzed, and found to contain 53.7 g./liter of tin. The solution contained 90.7% of methanol, and small amounts of toluene and organic by-products. Its pH was −0.13.

The methanol solution was added to a tank, and to it was added 908 kg. of dimethyl sulfoxide. The temperature of the solution rose 7° C. during the addition. After the DMSO was added, the suspension was stirred at ambient temperature for 2 days, and the solids were then separated by centrifugation in basket-type centrifuges. The solids were separated in 7 section, corresponding to the amount of solids which could be held in one centrifuge basket. The total amount of solids collected was 1,095 kg.

Samples of the solids were collected, and were analyzed. It was found that the solids contained 11.8% of volatile solvents, and 26.1% of tin.

The filtrate obtained from the centrifuging of the DMSO-stannic chloride complex was analyzed, and found to contain 1800 ppm. by weight of tin. The final pH of the filtrate was −0.14.

Example 6

Each of the experiments reported in this example was carried out by adding 250 ml. of the solvent named in the table below to a 500 ml. flask, adding a 12 ml. portion of stannic chloride to the solvent, and cooling the resulting solution to ambient temperature. Then a 25 ml. portion of DMSO was added over a period of about 15 seconds. The additions of DMSO were exothermic, and the temperature range observed is reported below. The mixture was stirred for 30 minutes, and vacuum filtered on fine filter paper. The filter cake was dried at 50° C. under vacuum and weighed.

| Solvent | Temperature Change | Yield, grams |
|---|---|---|
| acetone | 24–33° C. | 38.34 |
| methyl acetate | 24–40 | 41.43 |
| ethyl acetate | 24–40 | 42.73 |
| ethylbenzene | 24–53 | 40.06 |
| methyl isobutyl ketone | 24–35 | 39.32 |
| pentanol | 24–34 | 40.95 |
| methoxybenzene | 24–53 | 39.54 |
| chlorobenzene | 24–55 | 40.03 |
| isopropanol | 21–28 | 39.49 |
| benzyl benzoate | 31–46 | 32.39 |
| acetonitrile | 19–34 | 29.84 |
| nitromethane | 23–46 | 35.26 |
| 1/1 acetone/ethyl acetate | 24–36 | 38.40 |
| 3/1 methanol/toluene | 21–40 | 42.40 |

Example 7

A 2-liter flask was charged with 1250 ml. of methyl ethyl ketone and 60 ml. of stannic chloride. The solution was divided into five 250-ml. portions, each of which was placed in a 500 ml. flask. The solutions were allowed to cool to 24° C., and then an amount of DMSO, named in the table below, was added to each. The additions of DMSO were made as rapidly as possible. Each addition was exothermic. Each mixture was then stirred for 30 minutes, and filtered with vacuum. The filter cakes, consisting of the complex of DMSO and stannic chloride, were dried under vacuum at 50° C. for three days, and were then weighed.

| Volume of DMSO | Temperature Change | Yield, grams |
| --- | --- | --- |
| 5 ml. | 24–29° C. | 7.02 |
| 15 | 24–34 | 40.18 |
| 25 | 24–34 | 39.57 |
| 35 | 24–34 | 38.31 |
| 100 | 24–29 | 22.10 |

Example 8

Two solutions, each made up of 250 ml. of methanol and 12 ml. of stannic chloride, were treated with 25 ml. each of DMSO. In one case, the addition of DMSO was made at 23° C., and, in the other case, the addition was made at 60° C. In each case, the temperature of the mixture rose about 5° C. when the addition of DMSO was made. Each mixture was stirred at its constant temperature for 30 minutes, and was then filtered with vacuum, still at constant temperature. The yield of complex, after the filter cake had been dried for three days under vacuum at 50° C., was 40.99 g. in the 23° C. sample, and 40.10 g. from the 60° C. sample.

I claim:

1. A process for removing stannic chloride from solutions thereof in organic solvent-based waste streams, wherein the solvent is benzene mono-or disubstituted with $C_1$–$C_3$ alkyl, chloro, bromo, $C_1$–$C_2$ alkoxy or nitro; benzene monosubstituted with $C_1$–$C_5$ alkoxycarbonyl, benzyloxycarbonyl, phenoxycarbonyl or acetyl; $C_1$–$C_5$ alkanol; $C_1$–$C_4$ alkane monosubstituted with $C_2$–$C_5$ alkanoyl, nitro or $C_2$–$C_3$ alkanoyloxy; acetonitrile; or $C_5$–$C_8$ cycloalkanone; mixtures of said solvents; or a mixture of one or more of said solvents with a minor amount of a $C_5$–$C_{10}$ alkane; which process comprises adding to the waste stream from about 2 to about 4 moles of dimethyl sulfoxide per mole of stannic chloride, and separating the resulting precipitate of dimethyl sulfoxide-stannic chloride complex from the waste stream.

2. A process of claim 1 wherein the waste stream is at a temperature from about 0° C. to about 60° C.

3. A process of claim 1 or 2 wherein the solvent is benzene mono- or disubstituted with $C_1$–$C_3$ alkyl, chloro, bromo, $C_1$–$C_2$ alkoxy or nitro.

4. A process of claim 1 or 2 wherein the solvent is a $C_1$–$C_5$ alkanol.

5. A process of claim 1 or 2 wherein the solvent is $C_1$–$C_4$ alkane monosubstituted with $C_2$–$C_5$ alkanoyl; a $C_5$–$C_8$ cycloalkanone or acetophenone.

6. A process of claim 1 or 2 wherein the solvent is benzene monosubstituted with $C_1$–$C_5$ alkoxycarbonyl, benzyloxycarbonyl or phenoxycarbonyl; or a $C_1$–$C_4$ alkane mono-substituted with $C_2$–$C_3$ alkanoyloxy.

* * * * *